United States Patent

Mou et al.

[11] Patent Number: 5,957,580
[45] Date of Patent: Sep. 28, 1999

[54] METHOD FOR JUDGING APPLICABILITY OF INK-CONTAINING MEDIUM WITHIN INK CARTRIDGE

[75] Inventors: Tse-Chi Mou, Taipei Hsien; Yi-Jing Leu, Yunlin Hsien; Arnold Chang-Mou Yang; Ta-Wei Hsueh, both of Hsinchu Hsien; Li-Hsing Peng, Taitung; Ya-Hui Wang, Hsinchu, all of Taiwan

[73] Assignee: Microjet Technology Co., Ltd., Taiwan, Taiwan

[21] Appl. No.: 08/984,468

[22] Filed: Dec. 3, 1997

[51] Int. Cl.$^6$ ............................. G01N 25/00; G01N 5/02
[52] U.S. Cl. .................................. 374/14; 73/76
[58] Field of Search ................... 73/73, 76, 150 R; 374/14, 11

[56] References Cited

U.S. PATENT DOCUMENTS

| | | | |
|---|---|---|---|
| 3,813,918 | 6/1974 | Moe | 374/14 |
| 3,902,354 | 9/1975 | Harlan et al. | 374/14 |
| 4,165,633 | 8/1979 | Raisanen | 73/76 |
| 4,291,775 | 9/1981 | Collins | 374/14 |
| 4,753,889 | 6/1988 | Collins | 73/76 X |
| 4,798,252 | 1/1989 | Knothe et al. | 73/76 X |
| 4,817,745 | 4/1989 | Beshoory | 374/14 X |
| 5,002,399 | 3/1991 | Akinc et al. | 374/14 |
| 5,085,527 | 2/1992 | Gilbert | 374/14 |
| 5,588,746 | 12/1996 | Minobe et al. | 374/14 X |

Primary Examiner—Harshad Patel
Assistant Examiner—Robin C. Clark
Attorney, Agent, or Firm—Knobbe, Martens, Olson & Bear, LLP

[57] ABSTRACT

A method is provided for judging whether an ink-containing medium which is used for absorbing an ink is applicable to an ink cartridge. The method includes steps of (a) getting a first value A of a physical parameter of the ink-containing medium, (b) immersing the ink-containing medium into an ink container containing the ink under an immersion temperature for an immersion time, (c) washing the ink-containing medium, (d) drying the ink-containing medium under a dry temperature and a dry pressure, (e) getting a second value B of the physical parameter of the ink-containing medium, (f) calculating a relative change of the physical parameter of the ink-containing medium from the values of the physical parameters of the ink-containing medium, and (g) rejecting the ink-containing medium when the relative change of the physical parameter of the ink-containing medium is larger than a specific value.

19 Claims, 3 Drawing Sheets

METHOD FOR JUDGING APPLICABILITY OF INK-CONTAINING MEDIUM WITHIN INK CARTRIDGE

FIELD OF THE INVENTION

The present invention is related to a method for judging whether an ink-containing medium is applicable to an ink cartridge, and more particularly to a method for judging whether the stability of an ink-containing medium is applicable to an ink cartridge.

BACKGROUND OF THE INVENTION

An ink cartridge plays an important role in the ink jet printer. The ink jet printer can not work without an ink cartridge. The cartridge has an ink-containing medium therein for absorbing the ink. The ink-containing medium is usually a sponge which may be made from many different materials. When the sponge is pressed, a little amount of ink will flow into an ink-containing hole and then be ejected out the ink cartridge through a nozzle. The functions of the sponge within the ink cartridge are absorbing ink and controlling the flowing amount of ink. The sponge in the ink cartridge, undoubtedly, will be in contact with the ink for a long time. The performance of the sponge, however, will get worse and worse after a period of time. For example, dissolution of a portion of the sponge in the ink chokes the nozzle and hinders the printing operation. Another example is that the absorbability of the sponge also gets worse and worse, so it is anticipated to have a trouble of controlling the flowing amount of ink. An excellent ink jet printer should not be accompanied with such problems. There are many kinds of materials for manufacturing sponge in this field because material science has progressed greatly recently. Which kind of sponge is applicable to the ink cartridges of each kind of ink jet printers provided by different manufactures? The sponges made from the same material of different density also makes different performances. In order to be responsible for the performance of the ink jet printer, a simple stability test is needed before applying a new kind of sponge or a novel kind of ink. Moreover, when the manufactures buy a batch of sponges, stability tests of some random samples are necessary steps before adopting this batch of goods.

The conventional method for judging the sponge is to immerse it into ink for a long time and monitor the change of properties of the sponge. The change of properties of the sponge indicates that the properties of the sponge will change in the same manner when it is put into the ink cartridge. The less the change of properties is, the stabler the sponge is. The monitoring tests, however, spend much time because the lifetime of an ink cartridge is not a short period. Providing a simple and short-run method for judging sponge used in the ink cartridge will help the printer manufacturers to select applicable materials for the sponge.

SUMMARY OF THE INVENTION

An objective of the present invention is to provide a simple and short-run method for judging whether an ink-containing medium is applicable to an ink cartridge.

In accordance with the present invention, a method for judging whether an ink-containing medium which is used for absorbing an ink is applicable to an ink cartridge mounting therein the ink-containing medium, includes steps of (a) getting a first value A of a physical parameter of the ink-containing medium, (b) immersing the ink-containing medium into a ink container containing the ink under an immersion temperature for an immersion time, (c) washing the ink-containing medium, (d) drying the ink-containing medium under a dry temperature and a dry pressure, (e) getting a second value B of the physical parameter of the ink-containing medium, (f) calculating a relative change of the physical parameter of the ink-containing medium from the values of the physical parameters of the ink-containing medium, and (g) rejecting the ink-containing medium when the relative change of the physical parameter of the ink-containing medium is larger than a specific value.

In accordance with another aspect of the present invention, the relative change of the physical parameter of the ink-containing medium is defined as $$\frac{A-B}{A} \times 100\%.$$

In accordance with another aspect of the present invention, the physical parameter is a weight so the relative change of the physical parameter of the ink-containing medium is a solubility. Thus, the specific value is preferably 0.5%.

In accordance with another aspect of the present invention, the physical parameter is a maximum absorbability. Thus, the specific value is preferably 2%.

In accordance with another aspect of the present invention, the method certainly includes, before the step (a), a step of (a1) drying the ink-containing medium under another dry temperature and another dry pressure.

In accordance with another aspect of the present invention, the ink-containing medium is dried by a vacuum oven with dry temperature from 50° C. to 80° C. and with dry pressure 3.0 mmHg to 30 mmHg.

In accordance with another aspect of the present invention, the ink-containing medium is dried by a desiccant such as phosphorus pentoxide ($P_2O_5$), calcium chloride ($CaCl_2$), calcium sulfate anhydrite ($CaSO_4$), or magnesium sulfate ($MgSO_4$).

In accordance with another aspect of the present invention, the immersion temperature is from 50° C. to 100° C. and the immersion time is from 1 day to 5 days.

In accordance with another aspect of the present invention, the step (b) further includes a step of (b1) disturbing the ink for prompting the ink-containing medium to absorb the ink.

In accordance with another aspect of the present invention, the ink is disturbing by fixing the ink container on a rotary disc with a rotation speed from 50 r.p.m. to 150 r.p.m.

In accordance with another aspect of the present invention, the ink-containing medium is a sponge.

The present invention may best be understood through the following description with reference to the accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for the purpose of illustration and description only; it is not intended to be exhaustive or to be limited to the precise form disclosed.

Figure 1:
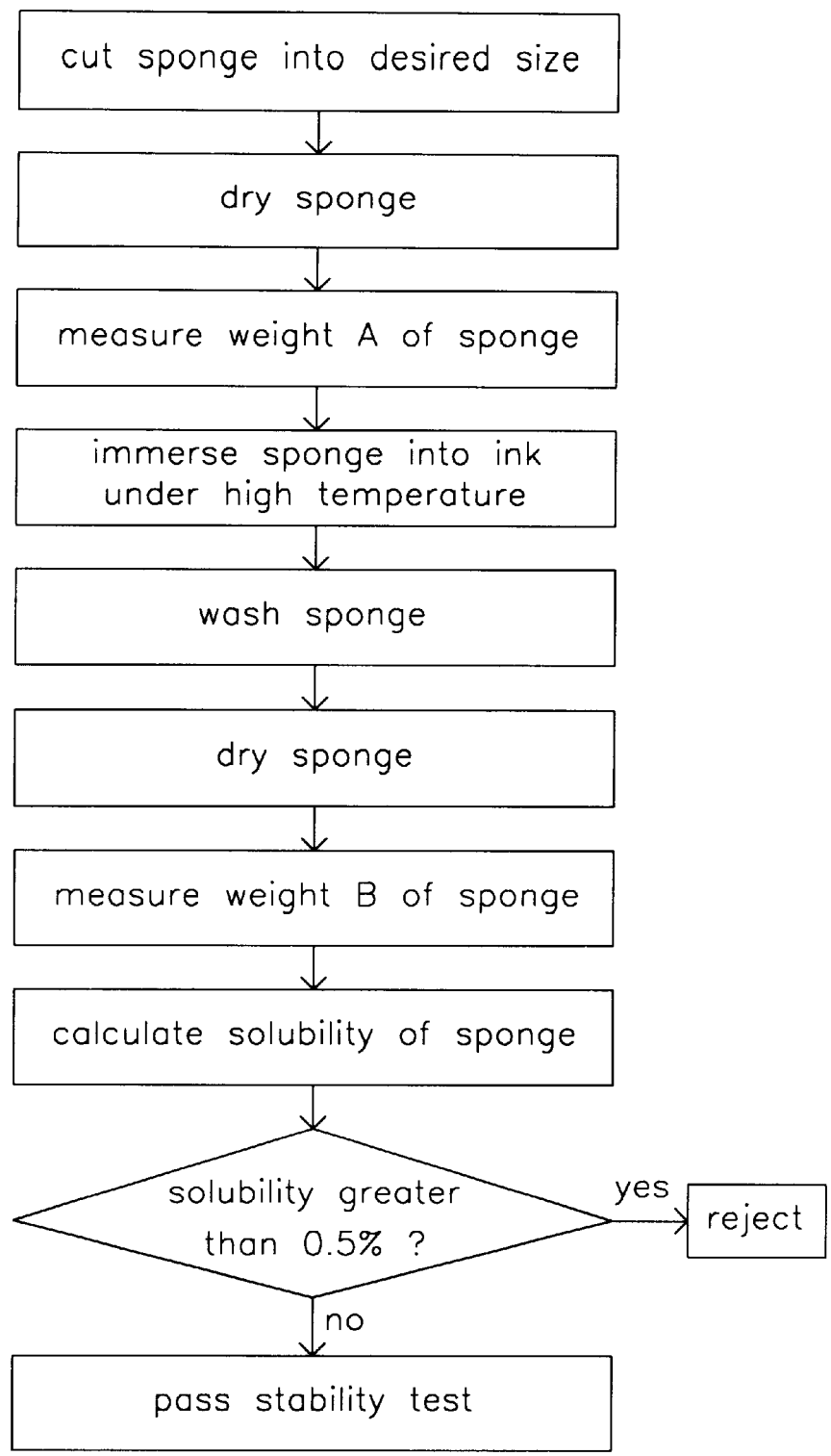
FIG. 1 is a flow chart showing a preferred embodiment of a judging method according to the present invention.

Please refer to FIG. 1 which is a flow chart showing a preferred embodiment of a judging method according to the present invention. The steps of the judging method are described as follows:

step(1) Cut a sponge into a desired size such as 34 mm×40 mm×60 mm.

step(2) Dry the sponge in a vacuum oven. The desiccant, 20 g phosphorus pentoxide, is put by the side of the sponge. The condition of the vacuum is set at pressure 3.0 mmHg and temperature 50° C. After 3 hours, take the sponge out the vacuum oven and then put it in a drier whose condition is set at room temperature.

step(3) Measure the weight A of the sponge after the sponge reaches room temperature.

step(4) Put the sponge into a 250 ml conical beaker, and add 200 ml ink into the conical beaker. Seal the conical breaker and fix it on the rotary disc of an incubator. The condition of the incubator is set at temperature 50° C. and rotation speed 80 r.p.m. for 72 hours to prompt ink absorption and aging of the sponge.

step(5) Take the sponge out and wash the sponge.

step(6) Repeat step (2). Dry the sponge in a vacuum oven which is set at pressure 3.0 mmHg and temperature 50° C. 20 g phosphorus pentoxide can be put by the side of the sponge to prompt removal of vapor. After 3 hours, take the sponge out the vacuum oven and then put it in a drier.

step(7) Measure the weight B of the sponge after the sponge is cooled down.

step(8) Analyze the data obtained from steps(1)–(7). Calculate the solubility $$\left(\frac{A-B}{A} \times 100\%\right)$$

of the sponge in the ink.

step(9) If the solubility of the sponge is greater than 0.5%, reject this kind of sponges or this batch of sponges because their stability is not good enough. If the solubility of the sponge is not greater than 0.5%, the sponge passes the stability test.

Undoubtedly, the less the solubility of the sponge is in the ink, the better the sponge is. Less solubility of the sponge indicates that the amount of the sponge dissolved in the ink may be neglected because no choking phenomena troubles manufacturers and users. The standard value of the solubility of the sponge must change according to precision and resolution of the equipment and one should not adhere to the specific value 0.5%. A specific value is given because it is appropriate to many kinds of existent ink jet printers. The solubility which is just less than 0.5% does not indicate that the sponge is applicable to all kinds of printers because some printers with higher resolution needs less solubility. On the other hand, if the solubility is greater than 0.5%, it does not indicate that the sponge is too bad to be used because it is acceptable for some kinds of printers with lower resolution.

Figure 2:
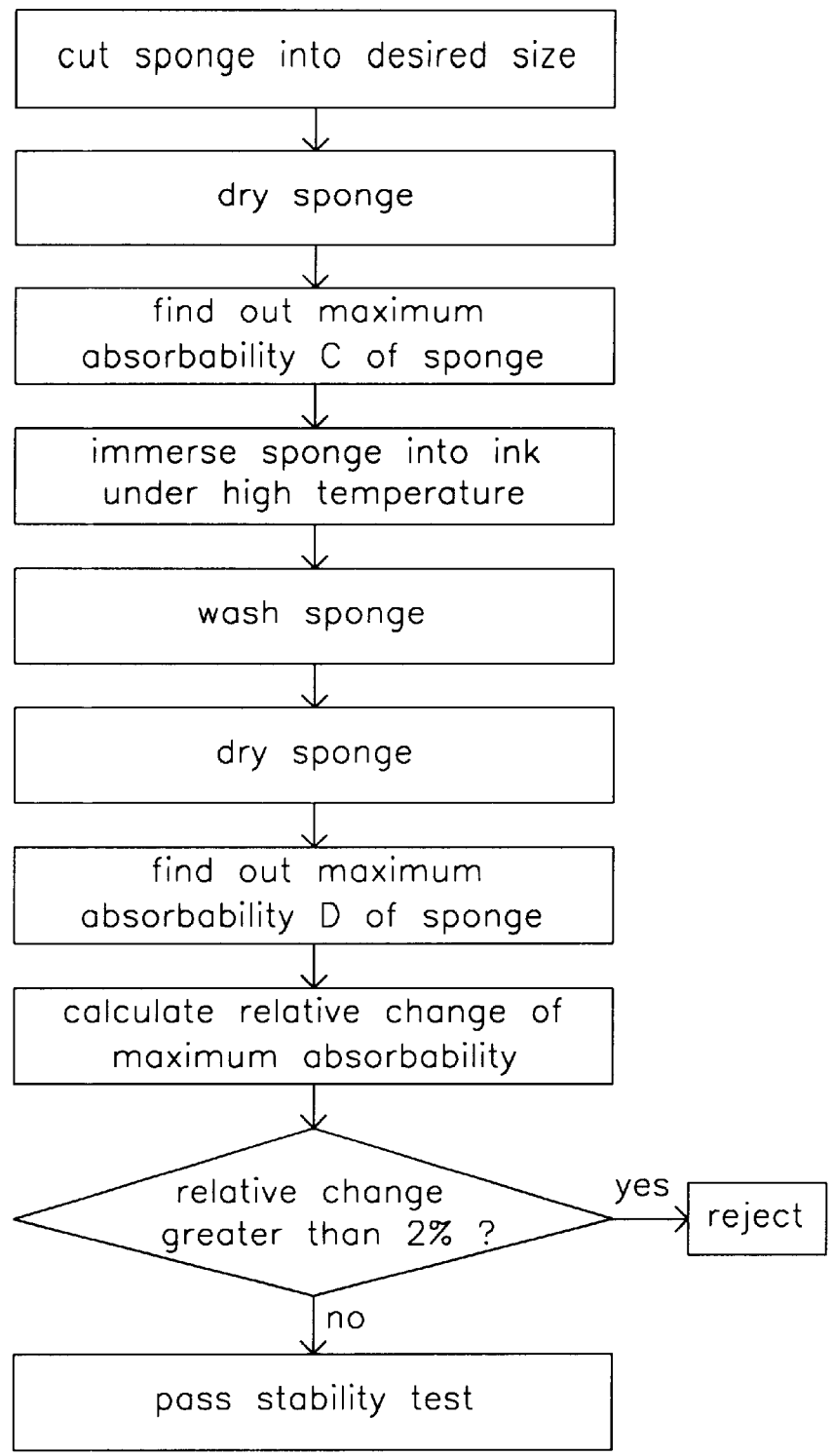
FIG. 2 is a flow chart showing another preferred embodiment of a judging method according to the present invention.

Another reference parameter can be applied to the invention. The process is similar to the prior embodiment. Please refer to FIG. 2 which is a flow chart showing another preferred embodiment of a judging method according to the present invention. The steps of the judging method are described as follows:

step(1) Cut a sponge into a desired size such as 34 mm×40 mm×60 mm.

step(2) Dry the sponge in a vacuum oven. 20 g phosphorus pentoxide is put by the side of the sponge. The condition of the vacuum is set at pressure 3.0 mmHg and temperature 50° C. After 3 hours, take the sponge out the vacuum oven and then put it in a drier set at room temperature.

step(3) Immerse the sponge into ink contained in a beaker to find out the maximum absorbability C of the sponge after the sponge reaches room temperature.

step(4) Put the sponge into a 250 ml conical beaker, and add 200 ml ink into the conical beaker. Seal the conical breaker and fix it on the rotary disc of an incubator. The condition of the incubator is set at temperature 50° C. and at rotation speed 80 r.p.m. for 72 hours to prompt ink absorption and aging of the sponge.

step(5) Take the sponge out and wash the sponge.

step(6) Repeat step (2). Dry the sponge in a vacuum oven. 20 g phosphorus pentoxide can be put by the side of the sponge to prompt removal of vapor. After 3 hours, take the sponge out the vacuum oven and then put it in a drier.

step(7) Immerse the sponge into ink contained in a beaker to find out the maximum absorbability D of the sponge after the sponge is cooled down.

step(8) Analyze the data obtained from steps(1)–(7). Calculate the relative change of the maximum absorbability $$\left(\frac{C-D}{C} \times 100\%\right)$$

of the sponge in the ink.

step(9) If the relative change of the maximum absorbability of the sponge is greater than 2%, reject this kind of sponges or this batch of sponges because their stability is not good enough. If the relative change of the maximum absorbability of the sponges is not greater than 2%, the sponge passes the stability test.

As it is described above, the less the relative change of the maximum absorbability of the sponge is in the ink, the better the sponge is. Less relative change of the maximum absorbability of the sponge indicates that the sponge has better ability to control the flow amount of ink flowing into ink-containing holes because no other uncertain factors will affect flowing of the ink out of the sponge. The standard value of the relative change of the maximum absorbability of the sponge must also change according to precision and resolution of the equipment and one should not adhere to the specific value 2%. The spirit and characteristics of the present invention should be noticed, but the specific value should not be used to limit the extent of the present invention.

Figure 3:
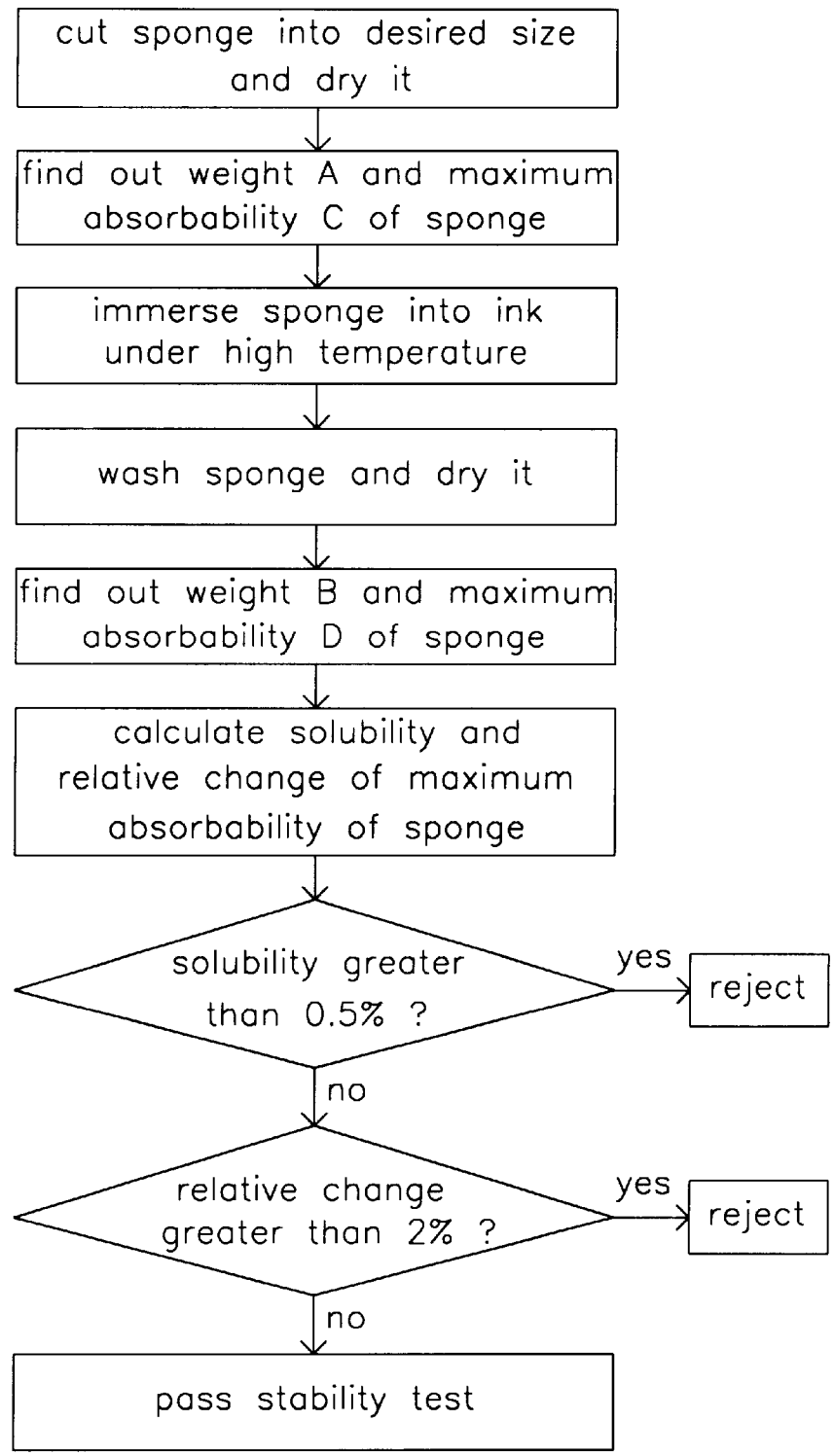
FIG. 3 is a flow chart showing a third preferred embodiment of a judging method according to the present invention.

The prior two preferred embodiments can be combined to double check the stability of the sponge. Please refer to FIG. 3 which is a flow chart showing a third preferred embodiment of a judging method according to the present invention. The steps of this preferred embodiment are similar to those of the prior two preferred embodiments, and are described briefly as follows:

step(1) Cut a sponge into size 34 mm×40 mm×60 mm. Then dry the sponge by a vacuum oven under pressure 3.0 mmHg and temperature 50° C. and by 20 g phosphorous pentoxide for 3 hours. Then, take it out and put it into a drier under room temperature.

step(2) Measure the weight A of the sponge. Next, immerse the sponge into ink to find out the maximum absorbability C of the sponge.

step(3) Immerse the sponge into ink contained in a conical beaker. Heat and shake the beaker to prompt ink absorption and aging of the sponge for 72 hours.

step(4) Take the sponge out and wash it. Then, dry the sponge as described in step (1).

step(5) Measure the weight B of the sponge. Next, immerse the sponge into the ink to find out the maximum absorbability D of the sponge.

step(6) Analyze the data obtained from steps(1)–(5). Calculate the solubility $$\left(\frac{A-B}{A} \times 100\%\right)$$

and the relative change of the maximum absorbability $$\left(\frac{C-D}{C} \times 100\%\right)$$

of the sponge in ink.

step(7) If the solubility of the sponge is greater than 0.5%, reject this kind of sponges or this batch of sponges.

step(8) If the relative change of the maximum absorbability of the sponge is greater than 2%, reject this kind of sponges or this batch of sponges, or the sponge passes the stability test.

The characteristics of the present judging method are that heating and disturbing the ink are executed while the sponge is immersed in. Such steps prompts aging of the sponge. In other words, these steps are used for simulating aging of the sponge in the ink in a short time. Two obvious judge parameters, solubility and relative change of maximum absorbability of the sponge, are introduced to show the stability of the sponge in ink. When the percentage of the dissolved sponge is too large, it chokes the nozzle of the ink jet printhead. Hence, the sponge is not stable enough. When the maximum absorbability changes too seriously, it is not favorable to control the ink flowing out. Hence, the sponge is not stable enough, too. These definite parameters are favorable to compare stability of different sponges in different ink. Compared with the prior art, the present judge method can save much time. Moreover, the method can be used to judge rapidly not only whether a newly developed sponge is applicable to the original ink within the ink cartridge, but also whether the original sponge is applicable to a newly developed ink within the ink cartridge. The easy method is useful for the manufactures to test an improved sponge or an improved ink. Besides, this method does not become more complex because it can be executed by simple experimental apparatus available in a conventional small laboratory. The superior potential is shown in low test cost and short test time.

In conclusion, a new method for judging whether a sponge is applicable in a cartridge is demonstrated and disclosed. The method is rapid, convenient, and easy enough to make itself utilizable.

While the invention has been described in terms of what are presently considered to be the most practical and preferred embodiments, it is to be understood that the invention need not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A method for judging whether an ink-containing medium absorbing an ink in an ink container is applicable to an ink cartridge mounting therein said ink-containing medium, comprising:
    (a) getting a first value A of a physical parameter of said ink-containing medium;
    (b) immersing said ink-containing medium into said ink container under an immersion temperature for an immersion time;
    (c) washing said ink-containing medium;
    (d) drying said ink-containing medium under a dry temperature and a dry pressure;
    (e) getting a second value B of said physical parameter of said ink-containing medium;
    (f) calculating a relative change of said physical parameter of said ink-containing medium from said values of said physical parameters of said ink-containing medium; and
    (g) rejecting said ink-containing medium when said relative change of said physical parameter of said ink-containing medium is larger than a specific value.

2. A method according to claim 1 wherein in said step (f), said relative change of said physical parameter of said ink-containing medium is defined as $$\frac{A-B}{A} \times 100\%.$$

3. A method according to claim 2 wherein in said steps (a) and (e), said physical parameter is a weight.

4. A method according to claim 3 wherein in said step (f), said relative change of said physical parameter of said ink-containing medium is a solubility.

5. A method according to claim 4 wherein in said step (g), said specific value is 0.5%.

6. A method according to claim 2 wherein in said steps (a) and (e), said physical parameter is a maximum absorbability.

7. A method according to claim 6 wherein in said step (g), said specific value is 2%.

8. A method according to claim 1 wherein before said step (a), said method further comprises a step of (a1) drying said ink-containing medium under another dry temperature and another dry pressure.

9. A method according to claim 8 wherein in said steps (a1) and (d), said ink-containing medium is dried by a vacuum oven.

10. A method according to claim 9 wherein said dry temperature is from 50° C. to 80° C.

11. A method according to claim 9 wherein said dry pressure is from 3.0 mmHg to 30 mmHg.

12. A method according to claim 8 wherein in said steps (a1) and (d), said ink-containing medium is dried by a desiccant.

13. A method according to claim 12 wherein said desiccant is selected from a group consisting of a phosphorus pentoxide ($P_2O_5$), a calcium chloride ($CaCl_2$), a calcium sulfate anhydrite ($CaSO_4$), and a magnesium sulfate ($MgSO_4$).

14. A method according to claim 1 wherein in said step (b), said immersion temperature is from 50° C. to 100° C.

15. A method according to claim 1 wherein said immersion time is from 1 day to 5days.

16. A method according to claim 1 wherein said step (b) further comprises a step of b1) disturbing said ink for prompting said ink-containing medium to absorb said ink.

17. A method according to claim 16 wherein said ink is disturbing by fixing said ink container on a rotary disc with a rotation speed.

18. A method according to claim 17 wherein said rotation speed of said rotary disc is from 50 r.p.m. to 150 r.p.m.

19. A method according to claim 1 wherein said ink-containing medium is a sponge.

* * * * *